United States Patent [19]

Gueyne et al.

[11] Patent Number: 5,087,452
[45] Date of Patent: Feb. 11, 1992

[54] THERAPEUTIC PRODUCT BASED ON AN ORGANIC COMPOUND OF SILICON AND POLYCARBOXYLATED POLYAMINE, PARTICULARLY USEFUL IN THE TREATMENT OF ATHEROMA

[76] Inventors: Jean Gueyne; Marie-Christine Seguin, both of Perigord 1, 6 Lacets Saint-Léon, Monte Carlo, Monaco; Gilbert H. Crussol, 19 Avenue Hoche, 75008 Paris, France

[21] Appl. No.: 503,989

[22] Filed: Apr. 4, 1990

[30] Foreign Application Priority Data

Apr. 7, 1989 [FR] France ............... 89 04577

[51] Int. Cl.⁵ ............... A01N 55/02; A01N 33/02; A61K 31/695; A61K 31/13
[52] U.S. Cl. ............... 424/422; 514/63; 514/667; 514/673; 514/724; 514/727; 514/738; 514/740
[58] Field of Search ............... 424/422, 667; 514/673, 514/724, 727, 738, 740, 824, 63

[56] References Cited

U.S. PATENT DOCUMENTS

| | | | |
|---|---|---|---|
| 4,707,360 | 11/1987 | Brasey | 424/94.1 |
| 4,985,405 | 1/1991 | Gueyne et al. | 514/8 |

FOREIGN PATENT DOCUMENTS

| | | |
|---|---|---|
| 0281435 | 7/1988 | European Pat. Off. |
| M6871 | 5/1969 | France |
| 955969 | 4/1964 | United Kingdom |

*Primary Examiner*—Thurman K. Page
*Assistant Examiner*—Carlos Azpuru
*Attorney, Agent, or Firm*—Ostrolenk, Faber, Gerb & Soffen

[57] ABSTRACT

Therapeutic product based on an organic derivative of silicon, particularly useful in the treatment of vascular diseases. The organic silicon compound is associated with a polyamine carrying hydrocarbon chains including carboxyl groups.

17 Claims, 1 Drawing Sheet

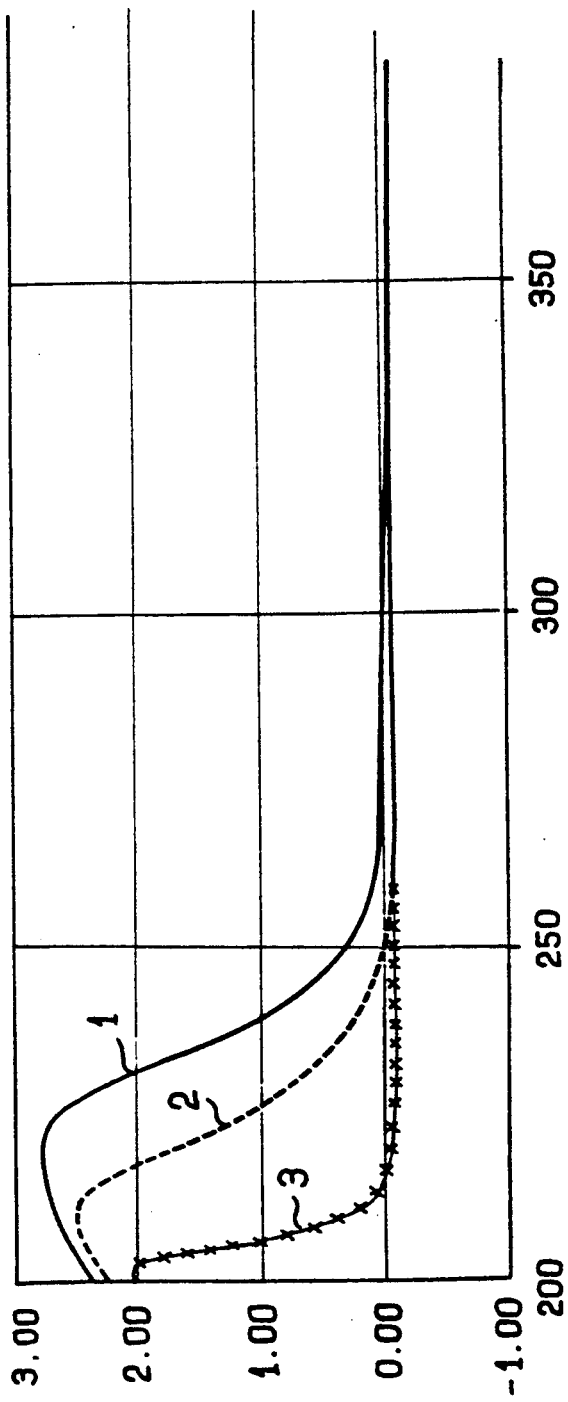

THERAPEUTIC PRODUCT BASED ON AN ORGANIC COMPOUND OF SILICON AND POLYCARBOXYLATED POLYAMINE, PARTICULARLY USEFUL IN THE TREATMENT OF ATHEROMA

The present invention relates to a therapeutic product formed by the association of an organic derivative of silicon with a polyamine carrying hydrocarbon chains including carboxyl groups. In particular, it includes associations in which the polyamine is a chelating agent of various metals and of calcium in particular. The therapeutic product is more especially in the form of an aqueous solution destined for parenteral administration in humans and animals. It is mainly useful in the treatment of various vascular diseases, particularly for the reduction of atheromatous plaques, inhibition of lipid peroxidation, stimulation of the regeneration of elastic fibers and normalization of cell metabolism.

Many medicinal substances have a veinotonic and vasoprotecting effect on the vascular system by reducing capillary permeability, and some exert a spasmolytic and/or vasodilating action. Among the substances used in this way, flavonoids, saponosides, rutins and other compounds with vitamin P activity, extracts of various plants, adenosine phosphate, naphthidrofuryl, buphenin, escin and others have been known for many years. In general, they improve the resistance of vessels but do not lead to regeneration of vessel walls. It was only in 1974 that a drug capable of stimulating the regeneration of conjunctive tissue appeared on the market. This advance, particularly important for the treatment of arteritis, was achieved by the use of silanols injected by I.V. or I.M. route. It thus became possible to regenerate arterial walls with about 20 to 40 injections of 0.05 g of methyl-silane-triol salicylate, at a rate of 2 injections per week, i.e. over a period of 10 to 20 weeks, but more often over a period of 6 months.

However, recent experience relative to the therapeutic applications of organic derivatives of silicon has revealed the completely unexpected fact that regeneration of conjunctive tissue can take place even more quickly and effectively if the silanol used is combined with an aliphatic polyamine carrying on its hydrocarbon chains several carboxyl groups, some of which may be neutralized by a metal cation.

This leads to the markedly improved result of allowing patients, whose vascular system could not be improved by any other treatment, to lead normal lives following a treatment of only 2 to 4 months. Moreover, the therapeutic product according to the invention is particularly well-adapted to administration by perfusion, which leads to much increased efficacy.

The product according to the invention, containing one or more silanols and/or siloxanes, is characterized in that this or these organic derivatives of silicon are associated with a compound of formula

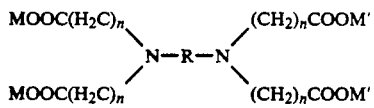  (1)

wherein n is 1 to 4, R is a $(CH_2)_m$ chain or

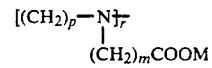

m being 1 to 12, p 2 to 4 and r 1 to 3 whereas M and M', similar or different, each represent a valency H or an alkaline or alkaline-earth metal or of Zn.

Preferably, the proportions of the reagents are such that there are 0.2 to 2 atoms of Si per carboxy-COO group in the product or, even more preferably, 0.3 to 1 Si per -COO group. The preferred form of this product is an aqueous solution.

Most often, the silicon compound is introduced into the solution according to the invention in the form of a salt of an alkaline or alkaline-earth metal, as it is in this form that a silanol or siloxane has to be taken up to be obtained in a non-polymerized form. The proportion of alkaline or alkaline-earth cation is 0.5 to 1.5 valencies per atom of Si and, more especially, 1 valency/Si atom.

For therapeutic applications, the aqueous solution according to the invention should be slightly acid. It is thus preferable that its pH range from about 3.5 to 6.5, and preferably from 5 to 5.5. It follows that, with reference to formula (1) given hereinabove, the number of H, M and M' cations varies in the solution, depending on the strength of the acid, such that the pH limits above are respected.

The following compounds are given as non-limiting examples of the most common polycarboxylated polyamines of formula (1) that can be used according to the invention:

E.D.T.A.-ethylene diamine tetra-acetic acid
R being $-CH_2CH_2-$ n=1

C.D.T.A.-trans-1,2-cyclohexane diamine tetra-acetic acid
R being

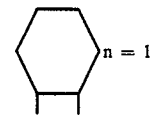

T.T.H.A.-triethylene tetramine hexa-acetic acid
R being

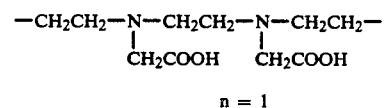

n = 1

D.T.P.A.-diethylene triamine penta-acetic acid
R being

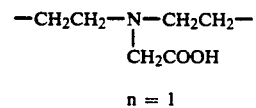

n = 1

The first of these compounds, E.D.T.A., is the most commonly used. It is mainly used in industry as a cation chelating agent. Its disodium salt is applied by intravenous route in the treatment of atherosclerosis. This salt acts by preventing the development and formation of atheromatous plaques but does not stimulate regeneration of arterial tissue. It is thus surprising to find that its association with a silanol or a siloxane leads to an accentuation of the regenerating effect of these organic compounds of Si.

The therapeutic solution according to the invention contains, as a silicon-containing compound, a silanol of the kind $R'_n Si(OH)_{(4-n)}$ wherein n is 1 to 3 and $R'$ is a hydrocarbon group, preferably a $C_1$ to $C_{18}$ alkyl and especially a $C_1$ to $C_6$ alkyl. On the other hand, the silicon-containing derivative can be a siloxane such as, for example,

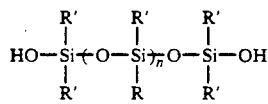

wherein $R'$ is a hydrocarbon group, preferably a $C_1$ to $C_{18}$ alkyl and n is a number from 0 to 20 and, preferably, from 0 to 4.

Although the concentration of the aqueous solution in polycarboxylated polyamine and silicon compound can vary within fairly wide limits, it generally ranges from 0.5 to 30 mmoles of polycarboxylated polyamine with 2 to 60 mmoles of silicon-containing derivative per liter, the molar ratio of these two kinds of associated compounds being conform with the values given above. In the particular case of the complex thus formed between E.D.T.A. and methyl silane triol, the weight concentrations in this complex range, for example, from 1 to 20 g per liter and preferably from 3 to 5 g/liter.

The therapeutic solution according to the invention, particularly the liquid for perfusion, can be prepared by mixing the two aqueous portions into which the polycarboxylated polyamine and the silicon-containing compound have been respectively previously stirred in or dissolved. The pH of the solution is then adjusted to the required limits using known means, namely by the addition of a soda solution, with continuous stirring. In order to avoid large changes in pH, it is advisable to adjust the pH of the polycarboxylated polyamine solution in advance to a value at least close to the pH value required at the end of the process. This may mean using an alkaline, alkaline-earth or zinc salt in which the carboxyl groups are partially neutralized by the corresponding cation.

An important condition for therapeutic application of the solutions according to the invention is the isotonicity of these solutions. This is why the molar concentration in silicon-containing complex and of any salts that may have been added is adjusted in such a way as to be equal to that of blood plasma in man or animals likely to receive the therapeutic solution.

Although the sole association of the two compounds according to the invention leads to regeneration of arterial and venous tissue, by cytostimulation of fibroblasts which produce good-quality elastic and collagen fibers, it is advisable (for pharmacological reasons) to include certain additives in the new therapeutic solution. It is thus advisable to add heparin, a local anaesthetic, such as lidocain or procain, vitamins, particularly ascorbic acid and the group B vitamins, trace elements and, as mentioned above, an electrolyte to ensure that the solution is isotonic if the concentration in molecules of the complex comprising the polycarboxylated polyamine-Si compound does not produce adequate osmotic pressure.

Depending on the condition of the patient to be treated, it may be useful, or even necessary, to add other therapeutic elements to the solution, compatible with the complexes according to the invention.

Whatever the case, even in the absence of other additives, the solution according to the invention exerts a lipolytic effect on vessels, leading to a reduction in atheromatous plaques. It has an inhibitory effect on lipid peroxidation, thus providing protection against the cytotoxicity of free radicals. As has already been mentioned above, an important advantage of this solution resides in the cytostimulating intensification of the silicon-containing compound. Further, normalization of cellular metabolism is produced.

The following formula is given as a non-limiting example of a formula for 1000 ml of solution according to the invention, particularly suitable for perfusions:

3 to 5 g of polycarboxylated polyamine/silanol complex
0.2 g of $MgCl_2$ or $MgSO_4$
0.2 g of lidocain or procain
1000 to 5000 units of heparin
4 to 20 g of ascorbic acid The form described hereinabove represents the form of the product most suitable for parenteral administration, in particular for perfusion. The product can nonetheless be presented in other forms: liquids, solids, pastes or emulsions. The characteristic all these forms have in common is the association of a polyamine of formula (1) with a silanol and/or siloxane.

The product can thus be stored and transported in the form of an aqueous solution of the complex according to the invention, keeping the undissolved carboxylated polyamine of formula (1) and the silanol and/or siloxane in suspension. This aqueous suspension can contain, for example, 5 to 20 times more active product than the definitive solution used in injections for patients. At the moment of use, it is diluted in distilled water to give a titre falling within the limits given hereinabove.

Another form the product according to the invention can be presented in is a powdered mixture of the two compounds, kept in an air-tight container. Ampoules or bottles, each containing a dose for injection, can also be used. The contents are dissolved in a set amount of distilled water, accompanying the ampoule or bottle, on administration of the drug.

The invention is illustrated in a non-limiting manner by the following examples.

EXAMPLE 1

Preparation of a therapeutc solution based on ethylene diamine tetra-acetic acid (EDTA) and monomethyl silane triol (MST)

6.4 g (21.9 mmoles) of EDTA in the form of a fine powder are dissolved in 500 ml of distilled water. 400 ml of aqueous solution of 3.5 g (37.2 mmoles) of $CH_3Si(OH)_3$ containing 37.2 mmoles of NaOH are slowly added, with continuous stirring. The pH of the mixture is adjusted to a value of 5 by the addition of an NaOH aqueous solution. The final volume is 2000 ml and contains $6.4 \pm 3.5 = 9.9$ g of EDTA-silanol complex. The Si/EDTA molar ratio is $37.2/21.9 = 1.7$. This corresponds to $1.7:4 = 0.424$ atom Si per COOH group of the EDTA used.

EXAMPLE 2

The operations are similar to those described in example 1, except that the EDTA used is in the form of its disodium salt at a concentration of 7.36 g (21.9 mmoles) and that 5.06 g (37.2 mmoles) of $C_4H_9Si(OH)_3$ were used instead of MST. The pH is adjusted to 5.08 and the volume of the mixture is completed to 2000 ml which thus contains $7.36 \pm 5.08 = 12.44$ g of silicon complex, the molar ratios being the same as in example 1.

EXAMPLE 3

Example 1 is repeated except that the methyl silane triol (MST) solution contains 46.5 mmoles (1.86 g) of NaOH. This means that at the end of the process, much less soda is needed to obtain a pH of 5.

EXAMPLE 4

The preparation is carried out in the same way as in example 3, MST being replaced by the same amount of dimethyl silane diol $(CH_3)_2Si(OH)_2$.

EXAMPLE 5

Therapeutic solution based on 1,2-cyclohexane diamine tetra-acetic acid (C.D.T.A.) and monomethyl silane triol 7.6 g (21.9 mmoles) of C.D.T.A. are dissolved in 500 ml of distilled water. 6.9 g (74 mmoles) of $CH_3Si(OH)_3$ are dissolved, with stirring, in 400 ml of water containing 3 g (75 mmoles) of NaOH. The total volume is completed to 2000 ml and the pH is adjusted to 4.9. A complex comprised of 3.38 moles of silanol per mole of C.D.T.A. is thus obtained, i.e. 0.844 atom of Si per COOH group in this tetracarboxylated diamine.

EXAMPLE 6

The solution is prepared in the same as in example 5, except that the silanol used is dimethyl silane diol.

EXAMPLE 7

The same process as in example 5 is followed except that the reagents used are:
triethylene tetramine hexa-aectic acid
T.T.H.A.-10.8 g (21.9 mmoles) and
dimethyl silane diol $(CH_3)_2Si(OH)_2$ 6.8 g = 74 mmoles.
Total volume 2000 ml. Final pH 5.1. 3.38 moles of silanol per mole of T.T.H.A., i.e. 0.56 atom of Si per —COOH group of T.T.H.A.

EXAMPLE 8

In the formula given in example 7, the silanol used is monoethyl silane triol $C_2H_5Si(OH)_3$ at a concentration of 15.6 g (144.5 mmoles). This represents 6.6 atoms of Si per mole of T.T.H.A. or 1.1 Si per —COOH.

EXAMPLE 9

The solution is prepared according to the process described in example 1, except that 21.9 mmoles (8.6 g) of diethylene triamine penta-acetic acid (D.T.P.A.) are used instead of 6.4 g of E.D.T.A. There is thus 0.34 atom of Si per —COOH group.

EXAMPLE 10

The composition of the solution per liter is 16 mmoles (6.3 g) of D.T.P.A. with 64 mmoles (5.9 g) of dimethyl silane diol $(CH_3)_2Si(OH)_2$. The silanol/D.T.P.A. molar ratio is 4, i.e. 0.8 atom of Si per —COOH group.

CLINICAL APPLICATIONS

Depending on the degree and nature of the disease, the mode of treatment, particularly the concentration in polycarboxylated polyamine/silanol or siloxane complex, and the mode of admininstration, in particular IM and IV injection or perfusion, can or should vary. In treatments which gave extremely favorable results, slow perfusions over periods of about 2 to 4 hours were carried out at a rate of 2 or 3 perfusions per week, the volume of liquid used being 500 to 1000 ml each time. This volume contained about 3 to 5 g of active complex in solution, in association with the additives mentioned above, before the examples.

In the treatments reported below, each perfusion was carried out with 5 g of complex in the volume mentioned in the report, also containing 0.2 g of $MgCl_2$, 0.2 g of lidocain, 10 g of ascorbic acid and 3000 units of heparin.

The order in roman numerals, initials, age and sex of each patient are mentioned at the top of each report.

I-P.M. 61 F

Patient suffering from angina pectoris. Treated with E.D.T.A. complex (the monomethysilane triol of example 1). 1. 2. 3. perfusion, 500 ml, lasting 4 hours, 4. 5. perfusion, 600 ml, lasting 3.5 hours, 6. 7. perfusion, 600 ml, lasting 2.5 hours, then thirteen 400-ml perfusions lasting 2 hours.

Progressive improvement with the disappearance of angina pectoris pains after the 8th perfusion.

A total of 20 perfusions in two months were carried out.

Improvement in hearing, as well as the end of a nasal mucoid discharge which the patient had been suffering from for the last 30 years following a bang on the head.

Doppler examination of the carotid arteries confirms the improvement reported by the patient. She no longer takes any drugs.

II-D.S. 64 F

Arteritis of the lower limbs. The patient presented herself at the clinic walking with great difficulty, even with a cane, despite 7 months of conventional treatment with naphthidrofuryl (Praxilene). She had recently been refused vascular surgery because of the bad condition of her arteries. Blood pressure had always been about 180/130. The patient appears 15 years younger after four months of treatment with T.T.H.A. complex (the dimethylsilane diol of example 7) at a rate of 500 ml per perfusion lasting three hours, once a week. She is now able to walk distances of over a kilometer alone and without a cane. Her blood pressure became stabilized around 140/100.

III-A.R. 53 M

Intermittent claudication with total blockage around the upper-thigh area (arteriography), despite 36 I.M. injections of Conjonctyl in 18 weeks.

Relative collateral circulation.

20 perfusions with C.D.T.A. complex (the monomethylsilane triol of example 5) are carried out. The first 5 perfusions are carried out every four days at a rate of 250 ml lasting 4 hours, the following 5 perfusions of 300 ml every three days for 3 hours and the final 10, every 3 days at a rate of 500 ml for 2.5 hours.

After 10 weeks of this treatment, a return to normal mobility is observed and the patient can climb stairs without difficulty.

IV-P.G. 58 M

Infarction and coronary bypass. High blood pressure followed by cerebral hemorrhage. Pessimistic Doppler flowmetry. Serious condition, despite 1 year of conventional treatment.

30 perfusions with E.D.T.A. complex (the dimethylsilane diol according to example 4) are carried out at a rate of two perfusions per week. Drugs are gradually reduced after the sixth perfusion and high blood pressure begins to decrease. After 4 months, an appreciable improvement Doppler flowmetry at the level of the carotid arteries is observed, tending towards normality. A relapse is unlikely.

V-B.K. 57 M

A cerebral hemorrhage 9 years ago left considerable paralysis in the right-hand side of the body.

Doppler flowmetry reveals a slowing down in blood flow at the level of the carotid arteries.

A series of 25 perfusions with T.T.H.A. (the monomethylsilane triol according to example 8) are prescribed, at a rate of 500 ml for 4 hours every day.

A marked improvement is observed at the end of the 6th perfusion.

Three months of treatment.

The patient is advised to start physiotherapy, as regeneration of nervous tissue appears to be possible following the improvement in vascularization.

VI-S.T. 82 F

Despite 1 year of conventional drugs, followed by 32 I.V. injections of Conjonctyl in 4 months, intermittent claudication allows this patient no more than 20 meters' autonomy.

Heart disease and important loss of potassium.

The posology of the previous example is instituted with D.P.T.A complex (the dimethylsilane diol according to example 10). A series of 25 perfusions are carried out at a rate of 500 ml for 4 hours every 4 days. Three months of treatment. Insufficient renal function allows no more than a half-dose of potassium to be administered during the first five perfusions. Renal function consequently improved. The patient has now doubled the distance she was previously able to walk.

VII-P.B. 55 F

Ankles are very swollen after only even a few steps. Obese although eating very little. Is constantly cold and lacking in energy. Doppler flowmetry detects only minute abnormalities in the carotid arteries. No particular examination of venous valves.

24 perfusions with 500 ml of C.D.T.A. complex (the dimethylsilane diol according to example 6) for 3 hours every 5 days lead to the elimination of water retention in the ankles. After four months of treatment, the patient lost weight and felt much better.

VIII-D.J. 63 M

After 16 months of treatment with Fonzylane, the patient still could not walk more than twenty steps without a violent pain forcing him to stop, both legs being equally affected.

24 perfusions with E.D.T.A. complex (the dimethylsilane diol according to example 4) are carried out at a rate of 400 ml every 3 days, for 3 hours.

The patient could walk 2 km two months after the end of this treatment.

IX-B.A. 58M

Arterial circulation in the legs is obtained only with assistance of cardial activity, despite Doppler flowmetry revealing an intact principal arterial system.

14 months of treatment with rutosides and 2 months with methyl silane triol salicylate had no effect on the condition.

400 ml of E.D.T.A. complex (the monomethylsilane triol according to example 2) are applied every two days for 4 hours, with a total of 20 perfusions.

Treatment lasted two and a half months.

After six perfusions, the patient was able to sleep for the first time following several weeks of insomnia. Doppler flowmetry shows a decrease in aortoiliac obstruction. Considerable improvement is observed in under two months of treatment.

X-B.R. 40 M

Heart surgery had been suggested to releave the patient of occasional but extremely violent angina pectoris.

Prescription of 25 perfusions of D.T.P.A. complex (the monomethylsilane triol according to example 10), 300 ml for 4 hours, every 4 days. Three and a half months of treatment but residual pains disappeared after the 14th perfusion (2 months).

XI-M.G. 79 F

Eye trouble, loss of balance, almost total loss of eyesight, loss of consciousness, general and constant feelings of discomfort make this patient's life unbearable.

Conventional treatment only led to slight and temporary improvement. Perfusions were started immediately, at a rate of 500 ml of T.T.H.A. complex (the monomethylsilane triol according to example 8) for 4 hours. As the patient was tired on the first day, the following perfusions were reduced to 250 ml, once a week for 3 months. At the end of this period, all the symptoms disappeared.

XII-H.A. 62 M

This patient is woken three times a night by angina pectoris pains. Conventional anti-angina drugs gave only temporary results.

Bi-directional Doppler flowmetry shows reverse flow which points to the aortic valve.

500 ml of T.H.A. complex (the dimethylsilane diol according to example 7) are administered for 5 hours, at a rate of two perfusions per week over a period of 4 months. After the second perfusion, nocturnal pains disappear and improvement in the diurnal symptoms begins after the 4th perfusion. Doppler examination at the end of treatment shows almost total normalization.

Animal Experiments

XIII

A 16-year-old gelding, which had just bitten a potential buyer, is saved from the slaughterhouse by his previous buyer after 7 years of work and ill treatment at an equestrian club in the Paris area; a tired, lame, belligerent, dangerous, unusable and sad horse. 4-hour perfusions with 1.5 liters of solution are applied twice a week for over three months, coupled to human presence and observation throughout the perfusion period.

Almost completely stops limping after the third perfusion. After the seventh perfusion, no longer limps, even when made to go round a narrow circle with a left-hand tether (the worst conditions for the horse's previous limp).

A total of 28 perfusions in three months are carried out using E.D.T.A. (the methylsilane triol according to example 3). The horse's health improved greatly and his training returned to a normal pace.

XIV 8-year-old gelding, had stopped participating in horse-races one year earlier, rebel limp defying all treatment. The horse stops limping, even when led round a narrow circle on the right-hand side, following treatment with the solution of example 5, which consisted of 24 perfusions in three months. This horse, which in addition to limping was also extremely lazy, now does 4 rounds of the paddock at a gallop whenever allowed to and races excellently, with courage. A young two-year-old stallion, with which he grazed without incident when he was ill, now attacks and bites him. He now has to put out to graze alone.

XV

A 7-year-old stallion, recently bought for a very high price following a favorable veterinary examination, begins to limp after his first race. The new owners, novices to the horse world, learn that the horse had been permanently drugged with anti-inflammatory drugs by his previous owner in order to be able to race. The pain is situated in the external part of the outer hoof, as shown by local anaesthesia.

It was observed from the very first perfusion that the sensitive left hoof was cold compared to the other hoof and remained cold during the first two hours of perfusion. It then became very hot and remained this way till the end of perfusion. In the following sessions, the difference in temperature gradually decreased and equalized, the temperature of the two hooves became constant.

This treatment, with the solution of example 8, comprised of 26 sessions in three months, very hard with a stallion, led to the remarkable result that the horse stopped limping and returned to normal work two months after the end of treatment.

XVI-L.A. 44 M

Hospitalized for stage II arteritis of the lower left limb. Is only able to walk some 150 meters. These problems began with the sudden appearance of intermittent claudication in the left calf.

Arteriography shows: on the right, important strain on the common iliac and thrombosis of the internal iliac on the left, almost total obstruction of the common iliac, thrombosis of the internal iliac and stenosis of the common femur.

3-hour perfusions are carried out over a period of 2 months, at a rate of one perfusion per week, using 500 ml of an aqueous solution containing 3.2 g of E.D.T.A. and 0.36 g of $CH_3Si(OH)_3$ per liter, adjusted to pH 5.

This solution is similar to the solution described in example 1, except that it contains only 0.088 atom of Si per —COOH group of the E.D.T.A. used.

After treatment lasting 2 months, the patient is able to walk 400–500 meters.

Another month of treatment does not lead to further improvements. It is decided to continue treatment for another two months with the solution of example 1, i.e. 0.424 atom Si per —COOH group under the same conditions as above.

The patient is thus able to walk without limitation, even in the case of strenuous effort, and the pulse is normal.

XVII-B.A. 72 M

Stage III arteritis of the two lower limbs. Is only able to walk some 150 meters, without decubitus pain but with small necrosed plaques at the level of the left foot.

Arteriography shows diffuse aorto-ilio-femoral strain with thrombosis of the internal ilia and bilateral femoro-popliteal thrombosis. A treatment of 500-ml perfusions of T.T.H.A. solution, similar to that in example 7 but with only 0.05 atom Si per —COOH group, is established at a rate of 3 hours, once a week.

The distance the patient is able to walk increases from 80 meters to 300 meters.

Treatment is continued for a month and the patient is able to walk 350 meters.

It is then decided to treat this patient for a month at the same rate as previously with the solution described in example 7, containing 3.38 moles of $(CH_3)_2Si(OH)_2$ per mole of T.T.H.A., i.e. 0.563 atom Si per —COOH group. The patient is now able to walk a distance of 850 meters. Furthermore, healing of necrosed plaques is observed.

Clinical reports XVI and XVII prove that really good results are obtained only when the solution used contains at least several tenths of Si atom per —COO group of the polycarboxylated polyamine used.

CHARACTERIZATION OF THE COMPLEXES ACCORDING TO THE INVENTION

The solutions, prepared in examples 1 to 10, were submitted to measurement of light absorption at various wavelengths. These measurements were carried out in comparison with those of solutions containing only the corresponding polycarboxylated polyamine or only the corresponding silanol. Measurements took place at room temperature. The apparatus used was that known under its commercial designation "KONTRON INSTRUMENTS ("UVIKON 930").

The attached graphs illustrate the relative variations in light absorption (ordinates) as a function of wavelength in nm (on the abscissae).

Graph 1 corresponds to the final solution of example 1, i.e. EDTA-silanol complex.

Graph 2 is that of an aqueous solution containing EDTA only at the same concentration as the solution in graph 1, i.e. 3.2 g/liter.

Graph 3 is obtained with a silanol $CH_3Si(OH)_3$ aqueous solution only, at the same concentration as solution 1, i.e. 1.75 g/l.

Marked differences in absorbance are noted. The values obtained for the complex formed, according to graph 1, are greater than those of graphs 2 and 3. A maximum is thus found for the EDTA-silanol complex (graph 1) around 220 nm. The maximum is situated around 210 nm, for EDTA alone (graph 2) and around 200 nm, for silanol alone (graph 3).

What is claimed is:

1. A therapeutic product which comprises a silanol or a siloxane and a polycarboxylated polyamine of the structure:

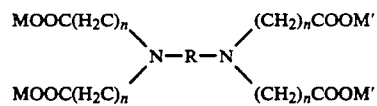

where n is 1 to 4, R is a $(CH_2)_m$ chain or

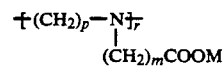

m being 1 to 12, p being 2 to 4 and r being 1 to 3, whereas each M and M' individually represents H, alkali or alkaline-earth metal or zinc, and the product contains at least 0.2 atom Si per carboxy group —COO.

2. Product according to claim 1 wherein it contains 0.2 to 2 atoms of Si per carboxy group.

3. Product according to one of claim 1 wherein the silicon containing compound is a silanol $R'_n$—Si$(OH)_{(4-n)}$ wherein n is 1 to 3 and R' is a hydrocarbon group.

4. Product according to claim 3 wherein R' is a $C_1$ to $C_6$ alkyl.

5. Product according to one of claim 1 wherein the silicon containing compound is a siloxane

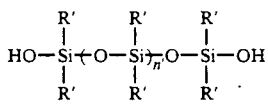

wherein R' is a hydrocarbon group, and n' is a number from 0 to 20.

6. Product according to claim 1 wherein it is in the form of an aqueous solution having a pH ranging from 3.5 to 6.5.

7. Product according to claim 6 wherein the aqueous solution contains 1 to 20 g of the, polycarboxylated polyamine+silicon containing compound per liter.

8. Product according to claim 6 wherein the aqueous solution is isotonic with blood plasma.

9. Product according to claim 8, wherein said liquid contains a mineral salt, a local anaesthetic, one or more vitamins and heparin.

10. Product according to claim 3 wherein R' is a $C_1$ to $C_{18}$ alkyl.

11. Product according to claim 5 wherein R' is a $C_1$ to $C_{18}$ alkyl and n' is from 0 to 4.

12. Product according to claim 6 wherein the pH is from 4 to 5.5.

13. Product according to claim 7 wherein the aqueous solution contains 3 to 5 g/l of the polycarboxylated polyamine+silicon containing compound.

14. Product according to claim 2 wherein the Si containing compound is a silanol of the formula $R'_{1-2}Si(OH)_{2-3}$ where R' is a 1 to 4 carbon atom alkyl and the polyamine is a diamine or triamine acetic acid or salt thereof.

15. Product according to claim 14 wherein the silanol is selected from the group consisting of monomethyl silane triol, dimethyl silane triol, ethyl silane triol, diethyl silane diol and butyl silane triol, and the polyamine is selected from the group consisting of ethylene diamine tetra-acetic acid, cyclohexane diamine tetra-acetic acid, triethylene triamine hexa-acetic acid, diethylene triamine penta-acetic acid and the alkali metal, alkaline-earth metal or zinc salts thereof.

16. Product according to claim 15 wherein it is in the form of an aqueous solution having a pH ranging from 3.5 to 6.5.

17. Product according to claim 16 wherein said liquid contains a mineral salt, a local anesthetic, one or more vitamins and heparin.

* * * * *